United States Patent [19]

Plewes

[11] Patent Number: 4,773,087

[45] Date of Patent: Sep. 20, 1988

[54] QUALITY OF SHADOWGRAPHIC X-RAY IMAGES

[75] Inventor: Donald B. Plewes, Rochester, N.Y.

[73] Assignee: University of Rochester, Rochester, N.Y.

[21] Appl. No.: 851,252

[22] Filed: Apr. 14, 1986

[51] Int. Cl.[4] .............................................. G21K 5/10
[52] U.S. Cl. .................................... 378/146; 378/108; 378/110; 378/112; 378/160
[58] Field of Search ................ 378/7, 13, 14, 16, 108, 378/110, 112, 145–147, 150.1, 160

[56] References Cited

U.S. PATENT DOCUMENTS

| | | | |
|---|---|---|---|
| 2,670,401 | 2/1954 | Weinberg | 378/146 |
| 2,837,657 | 6/1958 | Craig et al. | 378/146 |
| 2,962,594 | 11/1960 | Duffy, Jr. | 378/108 |
| 3,016,464 | 1/1962 | Bailey | 350/6.1 |
| 3,671,754 | 6/1972 | Mundkar | 350/272 |
| 3,766,387 | 10/1973 | Heffan et al. | 378/146 |
| 4,032,784 | 6/1977 | Rich | 378/112 |
| 4,243,325 | 1/1981 | Ernst | 350/272 |
| 4,259,582 | 3/1981 | Albert | 378/108 |
| 4,534,051 | 8/1985 | Grady et al. | 378/146 |
| 4,541,107 | 9/1985 | Rossi | 378/146 |
| 4,677,652 | 6/1987 | Duinker | 378/151 |

FOREIGN PATENT DOCUMENTS

| | | | |
|---|---|---|---|
| 0063644 | 11/1982 | European Pat. Off. | 378/108 |
| 2084829 | 4/1982 | United Kingdom | 378/146 |

OTHER PUBLICATIONS

Plewes, D. B., Computer-Assisted Exposure in Scanned Film Radiography, Proceedings International Workshop on Physics and Engineering in Medical Imaging, Mar. 1982, pp. 79–85.

Wandtke, J. C. and Plewes, D. B., Improved Chest Radiography with Equalization, RadioGraphics, vol. 3, No. 1, Mar. 1983, pp. 141–154.

Plewes, D. B., A Scanning System for Chest Radiography with Regional Exposure Control: Theoretical Considerations, Med. Phys. 10(5), Sep./Oct. 1983, pp. 646–654.

Plewes, D. B. and Vogelstein, E., A Scanning System for Chest Radiography with Regional Exposure Control: Practical Implementation Med. Phys. 10(5), Sep.-/Oct. 1983, pp. 655–663.

Plewes, D. B. and Vogelstein, E., Exposure Artifacts in Raster Scanned Equalization Radiography, Med. Phys. 11(2), Mar./Apr. 1984, pp. 158–165.

Primary Examiner—Craig E. Church
Assistant Examiner—John C. Freeman
Attorney, Agent, or Firm—Cooper & Dunham

[57] ABSTRACT

The quality of x-ray shadowgraphic images is improved by beam equalization controlled to ensure that just the right amount of radiation is used to accomplish the desired result, be it a desired image density and contrast or a desired signal-to-noise ratio or some other desired characteristic. The new techniques include: (1) maintaining a substantially constant signal-to-noise ratio throughout the image by measuring both scattered and primary radiation and using the results in a feedback loop to control the x-ray tube output, (2) raster scanning an x-ray beam along straight lines at constant velocity within a line by using a curved slit rotating aperture, (3) simultaneously controlling each of the intensity and hardness of a scanned x-ray beam as determined by post-patient x-ray measurements, and (4) using a segmented fan to scan the patient in a direction transverse to the plane of the fan and individually modulating each beam segment to achieve desired image characteristics.

18 Claims, 5 Drawing Sheets

QUALITY OF SHADOWGRAPHIC X-RAY IMAGES

BACKGROUND AND SUMMARY OF THE INVENTION

The invention is in the field of x-ray machines, such as those used for chest radiography and shadowgraphic radiography of other parts of a patient's body or of an inanimate object. Its main object is to improve image quality, for example by ensuring that just the right amount of radiation is used to accomplish a desired image characteristic, be it a desired image density or contrast or signal-to-noise (S/N) ratio or some other characteristic. For example, in imaging both lungs and mediastinum in a single picture, just the right amount of radiation can be delivered to achieve the required diagnostic content. The receptor can be conventional x-ray film or it can be some other receptor, such as a digital or a digitized receptor. The advantages of the invention include, in the case of film receptors, overcoming sensitometric limitations and, in the case of both film and digital receptors, control of S/N degradation from transmitted primary field variations, control of both the noise degradation and the nonlinear effects of scattered radiation, regaining low spatial frequency information lost initially by equalization, and reduction of exposure period and scanning artifacts.

Shadowgraphic radiography has been widely used for many decades, and has long-recognized inherent limitations. For example, chest radiography is probably the most frequently performed x-ray examination in a typical radiology department, and tens of millions of chest x-rays are taken annually in this country alone. However, in spite of its clinical importance it is far from being a technically consistent procedure and is subject to large variations in image quality, sometimes with imperfections in clinical results. One reason is that the posterior-anterior and lateral projections of the chest pose significant challenges. The presence of scattered radiation reduces film contrast, even when anti-scatter grids are used or an effort is made to reduce the scatter component by the use of air gap techniques or sophisticated anti-scatter grid designs. Scanning slit devices have also been used, bringing about significant contrast improvement in imaging the head, abdomen, chest and breast. Another inherent limitation in conventional chest radiography arises from the wide variation in patient x-ray thickness (meaning attenuation along a given raypath) between the lung field and the relatively thick mediastinal, retrocardiac and diaphragmatic portions, which produces a large variation in receptor exposure. One aspect of this is sensitometric, in that it may not be possible to achieve proper density or contrast at the portions of the image which may be of interest. Another deals with S/N ratios, in that the radiation reaching some portions of the receptor may be too little, in which case the S/N ratio can be too low, and that reaching other portions may be more than enough, in which case the patient would be exposed to more radiation than needed. Efforts to improve the exposure range of radiographic film with wide latitude films offer a wider exposure range, however at the expense of contrast in the lung fields, and with reduced signal-to-noise ratio over the thicker, underexposed portions. One approach to rectify these exposure problems is through the use of portal x-ray compensation filters shaped to match the contour of the lung fields and preferentially attenuate the pre-patient x-ray beam over the lungs, resulting in a more uniform film exposure. The obvious limitation is the difficulty of designing a filter to match the large variations in lung contour and patient thickness expected in a typical patient population. The so-called unsharp mask technique addresses this limitation by using a tailored optical filter for each patient, to be used in the film cassette during exposure. While these techniques can produce images with improved contrast uniformity, they can be time consuming and prone to misregistration artifacts in their clinial application. Digital radiography using arrays of detectors having wide dynamic range represents another imaging technique which offers good scatter rejection, image contrast control, and a potential for image data manipulation using temporal subtraction and multiple imaging techniques. However, in the systems known to the inventor herein these improvements are gained at the expense of spatial resolution, x-ray tube heat loading increase and an increased system complexity and cost.

Significant improvements have been made through the use of scanning equalization radiography using both prepatient and post-patient collimation to reduce scatter and a feedback technique to modulate a scanned x-ray beam. See, e.g.: Plewes, D. B., Computer-Assisted Exposure In Scanned Film Radiography, Proceedings International Workshop On Physics And Engineering In Medical Imaging, March 1982, pp. 79–85; Wandtke, J. C. and Plewes, D. B., Improved Chest Radiography With Equalization, RadioGraphics, Vol. 3, No. 1, March 1983, pp. 141–154; Plewes, D. B., A Scanning System For Chest Radiography With Regional Exposure Control: Theoretical Considerations, Med. Phys. 10(5), September/October 1983, pp. 646–654; Plewes, D. B. and Vogelstein, E., A Scanning System For Chest Radiography With Regional Exposure Control: Practical Implementation, Med. Phys. 10(5), September/October 1983, pp. 655–663; Plewes, D. B. and Vogelstein, E., Exposure Artifacts In Raster Scanned Equalization Radiography, Med. Phys. 11(2), March/April 1984, pp. 158–165. The contents of said publications are hereby incorporated by reference in the specification as though fully set forth herein.

Despite the significant progress made in the past in improving image quality, it is believed that room remains for improvement. In an effort to meet at least some aspects of this need, one of the features of this invention is to reduce signal-to-noise ratio variations in the x-ray image. One way of doing this in accordance with the invention is by measuring both post-patient scatter and post-patient primary radiation and using the results in a feedback loop controlling the pre-patient x-ray beam. One benefit is that the patient tends to be exposed only to the amount of radiation needed to produce an image of a given quality. Another is an overall improvement in image quality.

It has been proposed in the past, in the context of CT scanners, to ensure adequate signal-to-noise ratio by concurrently monitoring the integrated radiation from all of the detectors for a given x-ray pulse and ending the pulse only when all detectors have received at least a threshold quantity of radiation believed sufficient for an adequate signal-to-noise ratio. See U.S. Pat. No. 4,260,894. One of the many differences between this prior art proposal and this aspect of the invention disclosed and claimed here is that in the invention here each spot of the x-ray receptor should receive only the radiation sufficient for a selected signal-to-noise ratio, while in the prior art proposal it is only ensured that each CT detector would receive no less than the amount of radiation needed for a satisfactory signal-to-noise ratio (but in fact many detectors are likely to receive more, and thus expose the patient to more radiation than needed). Other proposals for modulating the pulse width of the pre-patient x-ray beam to achieve uniform film darkening are discussed in the publications authored or co-authored by Dr. Plewes, the inventor herein, cited above.

Another feature of the invention disclosed and claimed here is improving image quality by dynamically modulating each of the pre-patient intensity and pre-patient hardness of the x-ray beam on the basis of intermittent post-patient beam measurements made at selected positions of the beam relative to the patient and at a selected low beam intensity. It is generally desirable to use high KV (harder) radiation to reduce the dynamic range requirements on the receptor but to use low KV (softer) radiation in certain parts of the body (e.g., the lungs) to increase contrast. It is also generally desirable to use high intensity radiation through highly attenuating parts of the body (e.g., bone), so as to get sufficient radiation to the receptor, but low intensity through low attenuation parts of the body (e.g., lungs and soft tissue) to increase contrast. In this aspect of the invention disclosed and claimed herein, a very short pulse of low energy radiation and a very short pulse of high energy radiation are used at each selected beam position while scanning the patient. The relative amounts of bone and soft tissue along each beam are determined from those short pulses, and the best combination of intensity and hardness for that beam position is found and the x-ray tube is energized accordingly.

It has been proposed in the prior art (see U.S. Pat. No. 4,032,784) to control both the x-ray tube current and voltage in a raster scan x-ray machine so as to improve the picture and reduce radiation exposure. The patent proposes dynamically varying beam intensity to have high intensity through highly attenuating parts of the body and low intensity otherwise, and concurrently dynamically varying KV to have harder (shorter wavelength) radiation through high attenuation parts of the body and softer x-rays otherwise. However, the prior art patent proposes deriving the control signal from the output of the detector in the normal scanning operation rather than from short preliminary bursts of radiation. Another, similar prior art proposal is U.S. Pat. No. 2,962,594.

Another nonlimiting aspect of the invention relates to ensuring constant line velocity when raster scanning a patient through the use of a special, curved slit, rotating pre-patient collimator. While it is possible to use linearly moving collimator apertures (or an x-ray tube) to ensure constant line velocity (and thus facilitate modulation techniques) it is mechanically more efficient to use a rotating collimating aperture. This, however, introduces variation in the beam velocity within a raster scan line and complicates beam modulation.

A single x-ray beam can be raster scanned in overlapping scan lines to produce an x-ray image. This, however, must take several seconds, which can lead to motion artifacts. In order to reduce scanning time, and hence motion artifacts, another feature of this invention is to use a segmented fan beam scanned across the patient in a direction transverse to the plane of the fan. In accordance with a nonlimiting aspect of the invention, the fan segments are individually dynamically modulated to improve the image and reduce patient dosage. While there have been prior art proposals for using fans segmented by pre-patient or post-patient collimators, or both, as for example in the so-called localizer mode of CT scanners, and shaped collimators can be used to vary the pre-patient attenuation as between fan segments, the invention disclosed and claimed herein adds the benefit of dynamically and individually modulating the segments through a feedback loop.

There are at least two general application of equalization at this time, namely to x-ray film (nonlinear systems) and to wider dynamic range receptors, such as digital or digitized receptors. Especially for wider dynamic range receptors, the invention offers benefits such as control of signal/noise degradations from transmitted primary field variations, control of both the noise degradation and the nonlinear effects of scattered radiation, regaining low spatial frequency information lost by equalization and reduction of exposure period and of scanning artifacts.

With respect to control of signal/noise degradations from transmitted primary field variations, the objective is to maintain an approximately constant noise structure throughout the image, which implies approximately constant receptor exposure. Both primary and scattered radiation are important, and thus in accordance with the invention control can be maintained of both the noise degradation and the nonlinear effects of scattered radiation. While it is possible to use very narrow beam widths (e.g., 1 mm or less) to reduce scatter contamination, this may not be clinically practical because it places a severe load on the X-ray tube, as most of the radiation is blocked by the collimator. A more practical approach is to use a scanning beam which is a few cm wide, which cuts the X-ray tube load requirements but also increases scatter. Beam equalization in accordance with the invention offers two benefits in this respect. First, since the primary radiation levels at the receptor can be maintained approximately constant, the scatter/primary ratios will tend to be nearly constant. This can allow a measurement of scatter by looking beside the primary beam to be a good approximation of the full scatter profile. Thus, in accordance with the invention the scatter field can be measured while scanning to generate an approximate scatter field map which later can be subtracted from the initial image. This can make the scatter data more suitable for dual energy imaging and image processing techniques, which tend to be particularly sensitive to scatter contamination. This approach can allow a good approximation of the correction needed to account for the nonlinear effects of scatter, although the noise due to scatter would still be present. A second aspect of this approach is to use the scatter measurements made during the scan to adjust the x-ray tube output to compensate for the noise degradation from scatter.

With respect to regaining low spatial frequency information lost by equalization, it should be clear that one of the reasons equalization achieves improved images is that it rejects low frequency subject contrast. For example, the contrast between the mediastinum and the lung field is nearly eliminated by equalization. While this is useful in many, if not most, clinical situations, it can be troublesome in those where disease is manifest by low contrast variations that are diffuse and without sharp edges. Pneumothorax is a case in point. In this regard, the digital application of equalization can be particularly useful, because a record can be made during the scan of the spatial distribution of patient exposure. This information can then be used to correct the recorded data set to regain the lost low frequency information that would have been present in the uncorrected, equalized image. A simpler but less accurate way to do this is to normalize the measurements made for a one dimensional scan of the x-ray beam across the patient. If a fan beam is used, it is preferable to orient it vertically, i.e., to have its plane parallel to the mediastinum. Another way is to normalize the measurements for a two-dimensional scan. Here the two-dimensional distribution can maintain more accurately the noise uniformity over the image.

With respect to reduction of exposure period and scanning artifacts, a digital receptor can reduce the need for overlapping the scanning beams and thereby significantly reduce the exposure period. This can be done without very precise mechanical scan line registration, which is essential with film in order to prevent scan line artifacts, because with a digital receptor the line spacing can be made periodic and the scan line artifacts can be numerically filtered out.

Thus, in the case of digital receptors the features of the invention discussed above can lead to equalized images which are substantially free from scanning artifacts, can be produced in short exposure periods (e.g., of the order of 35–50 mS) to reduce motion blurring, can exhibit all desired low frequency structures and this can be applied to both one-dimensional and two-dimensional equalization systems, can have an approximately constant SN ratio, and can be free of significant scatter contamination.

These and other aspects of the invention are explained in greater detail in connection with the figures described below.

DETAILED DESCRIPTION

Figure 1:
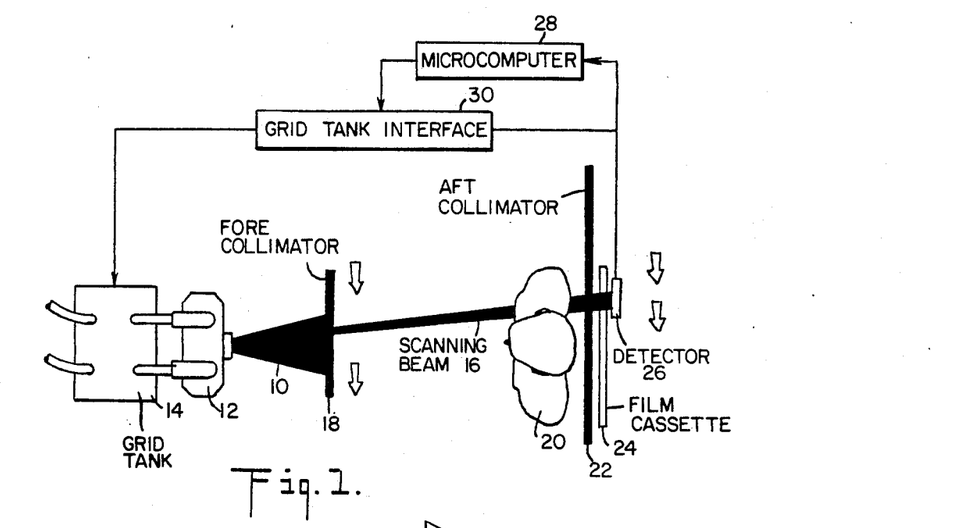
FIG. 1 is a schematic diagram of a scanning x-ray system to which certain aspects of the invention can be applied.

Referring to the schematic diagram of FIG. 1, an x-ray beam 10 comes from a source which comprises an x-ray tube 12 powered by a grid tank 14. Beam 10 is initially cone-shaped or pyramid-shaped, but is collimated to a scanning beam 16 by a pre-patient collimator (fore collimator) 18 to scan a patient 20 in raster fashion. A post-patient collimator (aft collimator) 22 sweeps the patient in synchrony with the pre-patient collimator such that scanning beam 16 scans a film cassette 24 (or some other receptor) in a raster of overlapping scan lines. A post-patient detector 26 receives radiation which has passed through receptor 24, and its output is used by microcomputer 28 to control grid tank 14 through interface 30 such that scanning beam 16 is modulated in a desired manner to achieve a desired result, for example in terms of image quality, SN ratio and/or patient dosage. Referring to the partial view of FIG. 2, a rotating wheel collimator 17 is between x-ray source 12 and pre-patient (fore) collimator 18 to collimate the cone- (or pyramid-) shaped x-ray beam 10 from source 12 into a fan 11, which in turn is collimated by the linear slit of collimator 18 into raster scanning beam 16 which can be, as a nonlimiting example, of a rectangular section of about 3.5×3.5 cm at the plane of receptor 24. Post-receptor detector 26, used in the feedback loop, can move with scanning beam 16, both along the raster lines and from raster line to raster line (as in FIG. 1), or it can be as long as a raster line so that it only need move from raster line to raster line with scanning beam 16 (as in FIG. 2). In the type of an x-ray system illustrated in FIGS. 1 and 2, scanning beam 16 can be modulated by dynamically varying its velocity along a scan line (velocity modulation) or by pulsing it at a selected frequency and at selected pulse widths (pulse width modulation or PWM) or by dynamically modulating its intensity and/or hardness or by dynamically modulating its shape (e.g., cross-section) or by a combination of sub-combination of the foregoing types of modulation. Some of those types of modulation are discussed in greater details in the publications authored or co-authored by Dr. Plewes, cited earlier and incorporated by reference.

Figure 3:
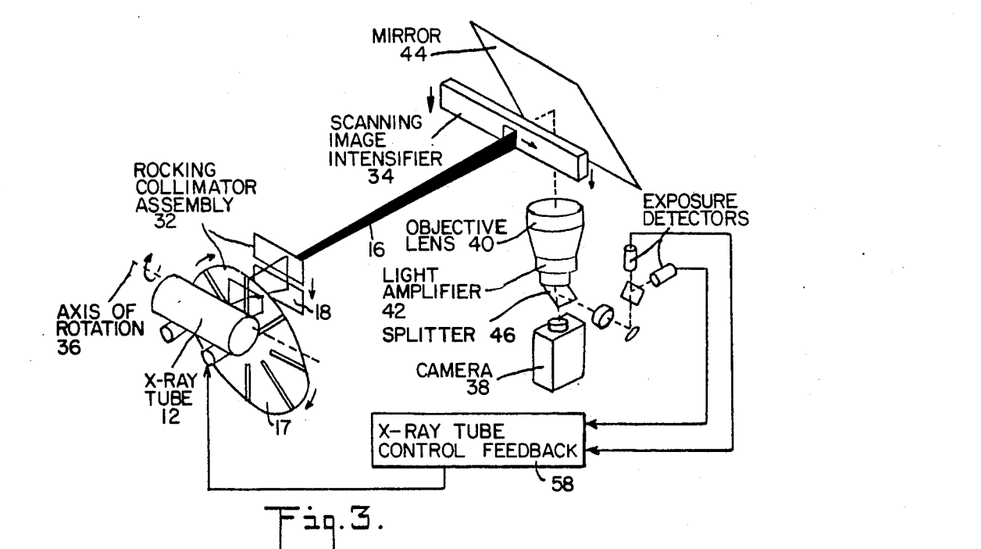
FIG. 3 illustrates the general layout of a system used in reducing signal-to-noise ratio variations in the image.

In accordance with one nonlimiting aspect of the invention, scanning beam 16 is modulated on the basis of post-patient measurements of both primary and scattered radiation through the use of a feedback loop to reduce variations in signal-to-noise ratio in the image. Referring to FIG. 3, the patient (not shown) is between pre-patient collimator assembly 32 and scanning image intensifier 34, and is scanned in a raster pattern of overlapping lines (actually strips) with scanning beam 16. Collimator assembly 32 comprises a rotating wheel collimator 17 and linear slit collimator 18. The entire unit comprised of x-ray tube 12, wheel 17 and collimator 18 rotates about axis 36 to move scanning beam 16 from one raster line to another. Scanning image intensifier 34 receives the post-patient part of scanning beam 16 and supplies some brightness gain relative to an unintensified phosphor, so as to preserve a large number of detected optical photons per absorbed x-ray photon after focusing through an optical system. In operation, x-ray beam 16 is scanned across the patient in overlapping raster lines and image intensifier 34 is scanned (moved relative to the patient) in synchronism, only in the direction transverse to the raster lines. During the scan, a video camera 38 views the portion of image intensifier 34 illuminated by scanning x-ray beam 16 through an objective lens 40 and a light amplifier 42. Camera 38 integrates the image on the photocathode of its video tube, which can be a Plumbicon. After the scan is complete, the charge pattern on the video tube photocathode can be read out in a slow scan, progressive mode to allow a spatial resolution of, e.g., 1024×1024 pixels.

Figure 4:
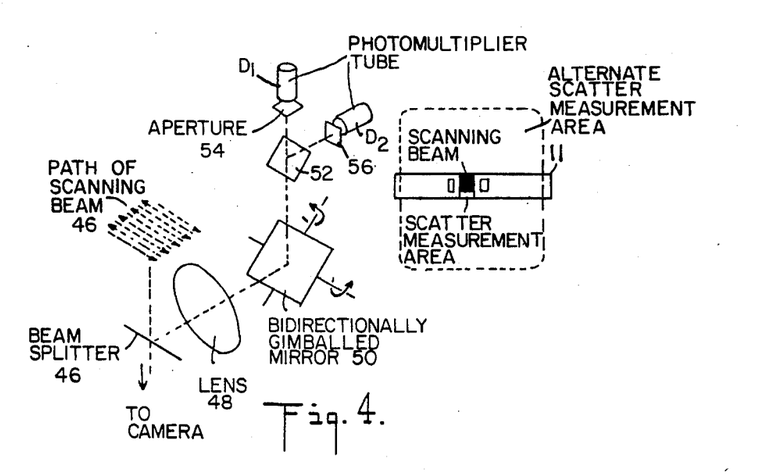
FIG. 4 illustrates an assembly to monitor primary and scattered radiation used in a feedback loop to reduce signal-to-noise ratio variations in the image.

Referring to the detailed view of FIG. 4, where the components corresponding to those shown in FIG. 3 bear the same reference numerals, the output of image intensifier 34 appears on mirror 44 as a path 46 of the scanning beam, and is viewed through objective lens 40 and light amplifier 42. A beam splitter 46 sends a part to camera 38 and a part to a bi-directionally gimbaled mirror 50 through a lens 48. Mirror 50 sends the optical image to a second beam splitter 52, which splits it into a part directed to a photomultiplier tube D1 and a part directed to a photomultiplier tube D2. Apertures 54 and 56 placed in front of photomultiplier tubes D1 and D2, respectively, are used to select respective portions of the scanning beam. The aperture for detector D1 is set to include measurements only over the area of scanning x-ray beam 16, to serve as an approximate measure of primary post-patient radiation, but the aperture for detector D2 is positioned to detect radiation reaching image intensifier 34 slightly off-axis of scanning x-ray beam 16, to serve as an approximate measure of scattered post-patient radiation. Thus, the two photomultipliers D1 and D2 provide a simultaneous indication of post-patient primary radiation as well as post-patient scattered radiation. Gimbaled mirror 50, splitter 52 and photomultipliers D1 and D2 and their apertures, move in synchronism with the path 46 of scanning beam 16 on mirror 44. The geometry of the scanning apparatus illustrated in FIGS. 3 and 4 is such that the presence of scattered radiation is low relative to that of conventional chest radiography, and can result in a scatter/primary ratio of 0.6 for a 2 cm² cross-section of scanning beam 16 with an absorber thickness of 20 cm. While this scatter contamination is not large, it still can reduce the detectability of low contrast details. In addition, the presence of optical scattering can add to x-ray scatter to degrade system contrast. This scatter represents a nonlinear contribution to projection data which can limit the use of some numerical processing techniques of interest to chest radiography. A point in case is the example of dual energy radiography, in which it is particularly desirable to avoid such nonlinear effects.

The presence of scattered radiation in conventional imaging is known to degrade image contrast, and also is known to play a role in reducing the image signal/noise ratio. It is believed that the image signal/noise ratio for low contrast objects in the presence of scattered radiation can be approximated by:

$$S/N = [N_0 A T n/(1+R)]^{\frac{1}{2}} \quad (1)$$

where $N_0$ is the incident photon fluence, T is the patient transmission, A is the pixel size, n is the detector quantum efficiency and R is the ratio of scattered to primary photons in the image. It should be noted that the scatter contribution a point in the image is the result of the total scatter over the image from all locations of the scanning beam. If a narrow scanning beam is used, scatter can be said to result from different positions of that beam along respective scan lines. Typically, the scatter field is a smooth, slowly varying distribution over the image field, so that scatter from different positions of the scanning beam along a given scan line tends to be roughly constant. Thus, the scatter measurement made by detector D2 for a given point in the image will tend to be approximately proportional to the scatter that would be contributed to that point from the other positions of the beam along that scan line. To get a measure of the scatter/primary ratio, the measurement from detector D2 should be normalized by that from detector D1. The result will only approximate the scatter/primary ratio, and can be scaled and calibrated to become a more accurate representation of the true scatter/primary ratio.

Relationship (1) above indicates that the signal/noise ratio is related to patient transmission such that in a scatter-free situation beam equalization would operate to keep the signal/noise ratio approximately constant throughout the image. However, in the presence of scatter, equalization on the basis of patient transmission alone would not ensure a constant image signal/noise ratio. Accordingly, in accordance with this aspect of the invention, a post-patient scattered radiation measurement corresponding to R is used in the feedback characteristics of the system. In practical terms, variations in T typically are much larger than the variations in R. However, the equalization technique in accordance with this aspect of the invention allows the noise degrading effects of scatter to be reduced or eliminated by considering the value R in system feedback. Thus, by the independent measurements of approximate scatter contribution and the scatter plus primary contribution attainable from detectors D1 and D2 in FIG. 4, it is possible in accordance with this aspect of the invention to calculate a value of R during the course of the scan and to use this value in a modified feedback relation. This is illustrated schematically in FIG. 3, where the outputs of exposure detectors D1 and D2 are supplied to x-ray tube control feedback device 58 which in turn controls x-ray tube 12 to vary $N_0$ (the incident photon fluence) in such a manner that the quantity S/N in equation (1) above remains substantially constant. In practice this can be implemented by a digital or an analog circuit arranged to derive the control signals needed to adjust $N_0$ in a manner which will maintain S/N constant in the relationship described by equation (1) above. The effect of this is to modulate scanning x-ray beam 16 through a feedback loop on the basis of post-patient measurements of primary and scattered radiation to reduce variations in signal-to-noise ratio in the image. This modulation is dynamic, as it is done on the fly during the raster scan movement of scanning x-ray beam 16.

In another aspect of the invention, the scatter measurements from detector D2, which looks only at the scatter measurement area shown in FIG. 4 below the scanning X-ray beam, can be used to generate an approximate scatter map, which can later be subtracted from the x-ray image, for example by using subtraction techniques such as used in digital subtraction radiography. This can give a good approximation of the correction needed to account for the nonlinear effect of scatter, although the noise due to scatter would still be present. If detector D2 looks only at the scatter measurement area below the scanning x-ray beam, as illustrated in FIG. 4, the gimbaled mirror arrangement is required only to scan the aperture for detector D2 in the scow scanning direction, i.e., from one scan line to another. As an alternative to using the scatter measurement area which is below the x-ray beam, the alternate scatter measurement areas which are in line with the x-ray beam can be used, as also illustrated in Fig. 4. In this case, the gimbaled mirror would need to track the fast motion of the x-ray beam along a scan line as well as the slow motion from one scan line to another. In this alternative, the aperture for detector D2 makes it look only at the illustrated alternate scatter measurement areas.

Another aspect of the invention pertains to simultaneously and dynamically modulating the scanning x-ray beam in terms of both intensity and hardness to improve image quality. This can be done on the basis of intermittent post-patient beam measurements made at select positions of the beam relative to the patient and at a selected low beam intensity. For example, a very short pulse of low energy radiation and a very short pulse of high energy radiation can be used at each select position of scanning x-ray beam 16, the attenuation along the beam for that beam position can be found and then the best combination of intensity and spectrum for that beam position can be calculated and the x-ray tube can be energized accordingly. The choice of an optimum beam spectrum for a given beam position is dependent on the interplay of patient dose, scatter contamination, tissue thickness and the resultant subject contrast. In considering chest radiography in particular, conflicting conditions influence this choice. In principle, it is desirable to maintain as low a beam energy as permissible by patient dose over the thinner portions of the lung, where soft tissue pulmonary markings are present, and thereby increase their subject contrast. However, the structures of interest in the mediastinum are mainly bony detail of the spine, which is intrinsically a high subject contrast structure, so that a low energy beam is not necessary. Furthermore, the thicker areas of the mediastinum would be better served with a more penetrating beam of radiation, since the dose for adequate exposure at low energies would be prohibitively large. The choice of optimum spectrum is further complicated by the presence of ribs over the thin lung field. While using a low kilovoltage beam over the lung zone can increase soft tissue subject contrast, it will also increase rib contrast to an even greater extent because of its thin atomic number. Thus, the net effect is that while soft tissue contrast can be improved, the greater attenuation from the ribs may degrade the visualization of soft tissue structures that are projected behind these ribs. Thus, because of the variation in structure thickness and atomic number, the optimum choice of beam energy for chest radiography is at best a compromise. These considerations, plus a desire to maintain visualization through the thicker body portions, have resulted in conventional chest radiography being routinely done at moderately high (120–140 KVP) kilovoltages in spite of the loss of subject contrast for soft tissue.

It is possible in accordance with the invention to vary the beam intensity and kilovoltage continuously over the anatomy to maintain an optimum beam kilovoltage and exposure for maximum soft tissue contrast throughout the entire anatomy. A relatively simple implementation can be to monitor post-patient radiation for each selected position of the scanning x-ray beam as a clue to the structure being imaged. This parameter can then be used to modulate beam kilovoltage in a predetermined fashion. Film intensity equalization, e.g., by the use of pulse width modulation as described in the papers cited earlier, can be done simultaneously to ensure maximum film contrast. This requires that for each x-ray pulse the duration and kilovoltage need to be controllable. A reasonable relation between patient transmission and kilovoltage is to use a low kilovoltage over the lung fields and continuously shift to a higher kilovoltage over the thicker body parts. By this means, both the intensity and kilovoltage of the scanning x-ray beam can be modulated over the patient to avoid the kilovoltage compromises that currently limit conventional chest radiography and increase soft tissue contrast beyond that of simple intensity-modulated techniques. By changing beam kilovoltage over the anatomy as just described, significant improvements in soft tissue contrast can be obtained. However, this relatively simple implementation of variable kilovoltage can show degraded contrast due to rib shadowing for reduced kilovoltage over the lung fields. In this method the ribs will be represented as local areas of moderately decreased transmission and will not be handled any differently from any other structural variation. However, if knowledge of the location of the ribs were available, the beam kilovoltage can be locally increased over the area of the ribs to avoid the undesirable consequences of rib shadowing.

One approach to this problem in accordance with the invention is to use a two-scan approach: a pre-scan immediately followed by a second scan forming the desired image. The first scan obtains a low resolution transmission distribution of the patient. This can be done using very short pulses of radiation (e.g., 25 microseconds per pulse) that would not contribute significantly to patient dose and are inadequate to expose the film or other receptor. This transmission map can then be used to determine the position of the major structures such as the mediastinum, abdomen, heart and lung contours. In addition, using edge detection methods the positions of the ribs in the lung zones can be located. This information can then be used in the second, immediately following scan of the patient, which exposes the film or other receptor. Of course, the delay between the first and second scans, although of only a few seconds, can lead to registration problems because of patient movement.

Accordingly, in accordance with another feature of the invention, these registration problems are reduced or eliminated by a dual energy method to locate the ribs in the lung field. In accordance with this aspect of the invention, two short pre-exposure pulses of widely different kilovoltage (e.g. 120 and 80 KVP) are used, followed by a longer pulse of a duration which exposes the receptor for that position of the scanning x-ray beam. The pre-exposure pulses are short enough to give only negligible receptor exposure, and are used to determine the projected density of bone and tissue, using dual energy algorithms similar to those discussed by Alvarez and Rutherford for dual energy CT and Brody for dual energy chest radiography applications using the techniques referred to in the earlier-cited literature. The kilovoltage for the imaging pulse can then be determined from the pre-exposure pulses while the duration of the imaging pulse (i.e., the integrated beam intensity) can be determined to equalize image density. By this dual energy means, the amount of bone at each selected position of the scanning x-ray beam can be measured during the scan, and a predetermined lookup table adjustments of beam kilovoltage can be made to minimize rib shadowing artifacts directly.

Figures 5, 6:
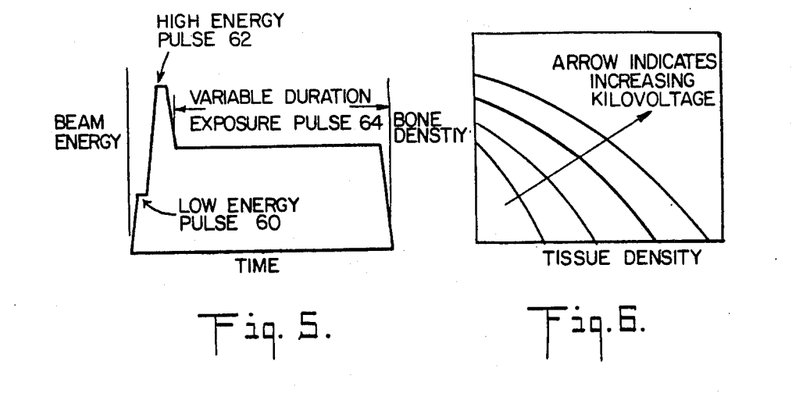
FIG. 5 is a graph of beam energy versus time relating to dynamically modulating each of the pre-patient intensity and pre-patient hardness of the x-ray beam.
FIG. 6 pertains to modulating pre-patient hardness of the x-ray beam.

Referring to FIGS. 5 and 6, at each selected position of scanning x-ray beam 16 along the raster scan lines, the x-ray tube is energized for a short, low energy pulse 60, immediately followed by a similarly short but higher energy pulse 62, follwed by an exposure pulse 64 of a variable duration determined as discussed in said articles authored or co-authored by Dr. Plewes, for uniform receptor exposure. The kilovoltage of exposure pulse 64 is determined on the basis of a continuous relation such as illustrated in FIG. 6, which shows the lines of constant kilovoltage of x-ray tube 12 as a function of bone and tissue density. Such a relation continuously raises the x-ray tube potential over areas of either large tissue thickness or lung rib areas and shift toward lower kilovoltages in regions of lung field where little bone is present. By the choice of this function the rate at which the tube kilovoltage is raised is a function of bone and tissue density is programmable.

To accomplish independent control of the x-ray tube kilovoltage, a tetrode switching apparatus can be fitted to an x-ray tube high voltage generator. This device is a pair of voltage regulators for the cathode and anode lines in the secondary line of the x-ray generator high voltage transformer, and allows precise kilovoltage control. The same device is capable of switching the x-ray beam on and off as can alternately be accomplished with grid control. The tetrode switching apparatus thus can allow for simultaneous and dynamic pulse width and beam kilovoltage modulation of the scanning x-ray beam. A particular tetrode switch can control the tube kilovoltage between 50 and 140 KVP and pulse the x-ray beam at frequencies of up to in excess of 2,000 Hz.

Figure 2:
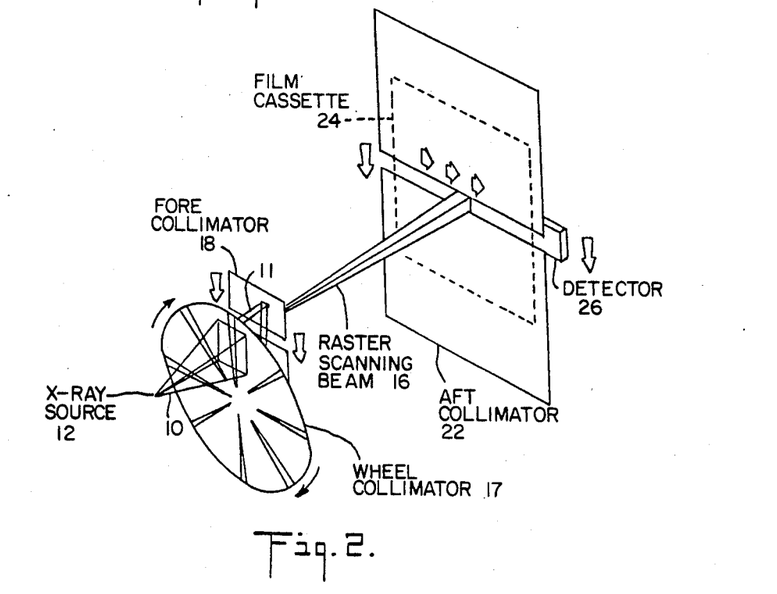
FIG. 2 is a perspective view of certain components of the scanning x-ray system of FIG. 1.

In the systems illustrated in FIGS. 2 and 3 the rotating wheel collimator 17 has apertures in the form of straight radial slits which, in combination with the aperture in the form of a linear slit in pre-patient collimator 18, scan x-ray beam 16 along successive, overlapping scan lines. In this geometry the scanning velocity of x-ray beam 16 along the receptor is not constant; the velocity decreases slowly from the extreme end of a scan line toward its center and then increases toward the other extremity of the scan line. This variation in velocity must be accounted for in modulating the scanning x-ray beam. In order to avoid increasing the complexity of the modulating technique because of such velocity variation, a linearly scanning aperture can be used, or the entire x-ray tube can be scanned with respect to the patient. This, however, introduces mechanical complications. Velocity variations can also be decreased by the use of a large wheel collimator with a relatively large number of aperture slots. This again introduces mechanical complications.

Figures 7, 8:
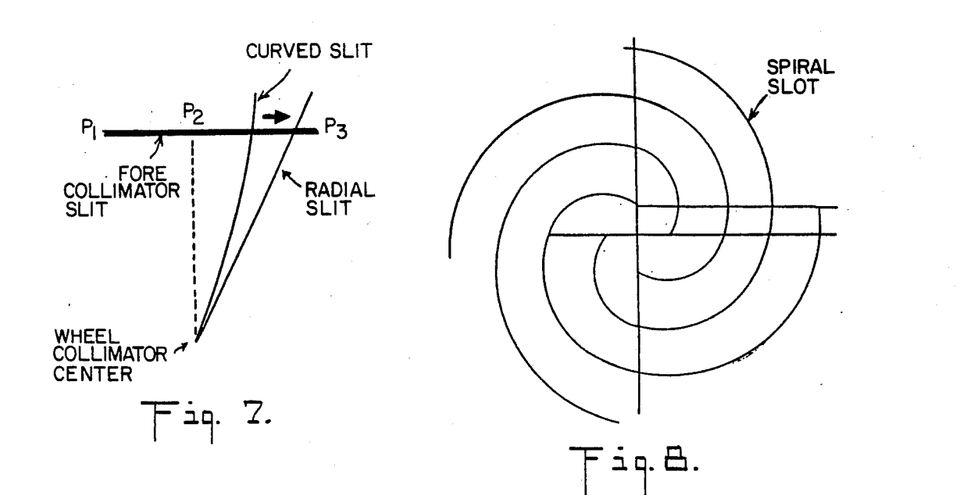
FIG. 7 illustrates scanning x-ray beam velocity along a scan line in the case of a radial slit collimator as compared to a curved slit collimator.
FIG. 8 illustrates four angular positions of a rotating, curved slit collimator.
Figure 9:
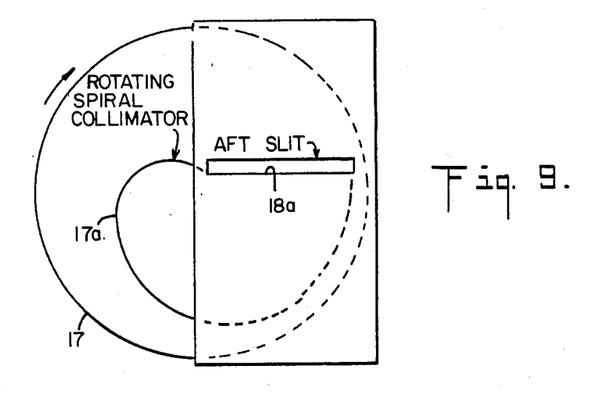
FIG. 9 is another illustration of a curved slit collimator superimposed on a linear slit collimator.
Figure 10:
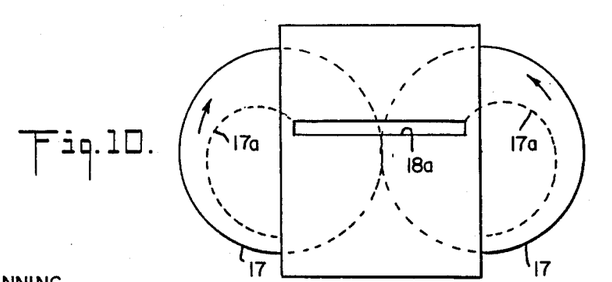
FIG. 10 illustrates two counter rotating, curved slit collimators superimposed on a linear slit collimator.

In accordance with another aspect of the invention, the velocity of the scanning x-ray beam along a scan line is kept substantially constant through the use of a novel wheel collimator which is small in diameter and uses a uniquely curved aperture slit. As illustrated in FIG. 7, if a rotating wheel collimator 17 with a straight radial slit is used, for a fixed rotation rate the horizontal scanning x-ray beam velocity will be variable since the radius of the collimator slit projecting the beam increases as it moves toward the scan line limits. Thus, the velocity increases toward the scan line ends P1 and P3. However, when the wheel slit is curved as shown in FIG. 7, and restricts the scan line to be between P2 and P3, the curved slit causes the horizontal position of the scanning x-ray beam to fall progressively behind the corresponding position of the radial slit, thereby reducing the scanning x-ray beam velocity toward the point P3. A rotating wheel collimator 17 with a single spiral slit can scan the x-ray beam over a scan line in a single rotation. This spirally curved slit is shown in FIG. 8 at four different 90° intervals as it intersects the pre-patient collimator 18. As the wheel collimator moves through successive 90° increments, its intersection with the linear slit in collimator 18 moves the x-ray beam through constant linear intervals, indicating its constant velocity. FIG. 9 is another illustration of a rotating wheel collimator 17 with a spiral aperture slit 17a superimposed on the linear slit 18a of pre-patient collimator 18. FIG. 10 illustrates a variation, in which two counter rotating collimator wheels 17 having curved aperture slits 17a are used to scan x-ray beam 16 with respect to the linear aperture 18a of the pre-patient collimator. It should be noted that similar combinations of rotating wheel collimators with curved aperture slits and collimators with fixed linear slits can be used between the patient and the film or x-ray detector but, of course, would have to be proportionately larger in size than the pre-patient collimators, and would have to be synchronized with the pre-patient collimators so that the x-ray beam 16 passes through aligned apertures in the pre-patient and post-patient collimators before reaching the receptor.

Figure 11:
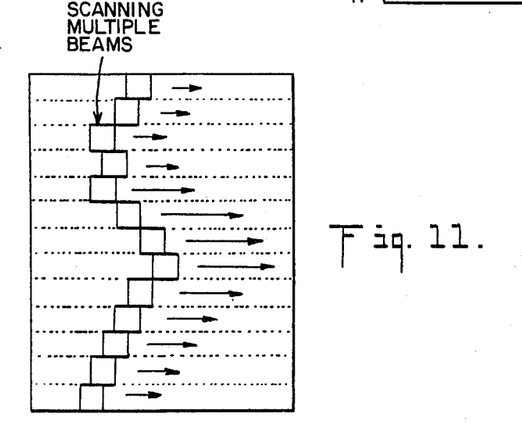
FIG. 11 illustrates scanning multiple beams.
Figure 12:
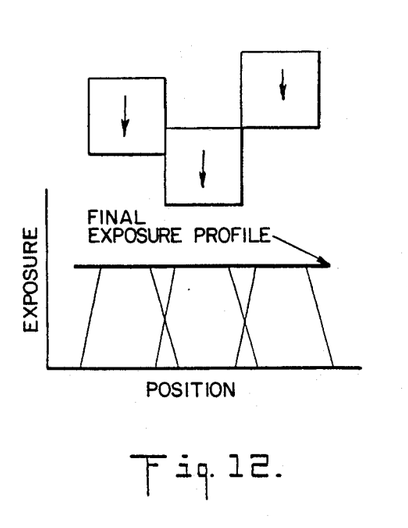
FIG. 12 illustrates exposure overlap by three scanning x-ray beams moving at the same velocity.
Figure 13:
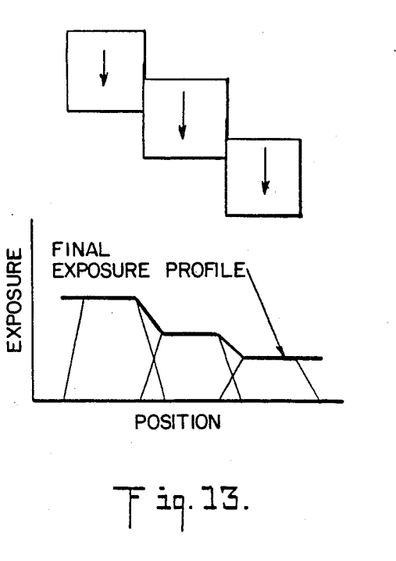
FIG. 13 illustrates exposure overlap by three scanning x-ray beams moving at different velocities along respective scan lines.

In the embodiments discussed above, a single scanning beam 16 is used to scan the patient in overlapping scan lines. This can expose the receptor for a typical chest x-ray in about 3-5 seconds, during which time some motion artifacts may become apparent. In order to reduce exposure time, a fan beam divided into a number of segments can be used, each segment in effect scanning its own scan line, and with a number of scan lines scanned simultaneously. This is illustrated in Fig. 11, where a number of segments, each represented by a respective square, scan along respective horizontal scan lines indicated by respective arrows. If velocity modulation is used, then each segment can be considered an individual scanning beam and can be individually velocity modulated, in the manner discussed for velocity modulation of single beam systems in said publications. If the pre-patient collimators producing the individually scanned segments of the fan beam are placed close to the x-ray focal spot, then their exposure profiles on the film or image intensifier will be blurred or overlapped, as illustrated in FIG. 12. If the segments are moving at the same speed across the patient, and the adjacent apertures for the segments are such that their edges are collinear, then the blur of adjacent scan lines will combine to produce a substantially uniform exposure, as illustrated in FIG. 12. However, if the beams are moving at different scan line velocities, then the receptor exposure from each scan line will differ, and the transition between adjacent scan lines will be rendered as a smooth gradation, as illustrated in FIG. 13. A conventional scatter rejection grid can be used in place of a rotating post-patient collimator in the system discussed in connection with FIGS. 11-13. If a fan beam is divided into three segments, in an exemplary test system, three pre-patient scanning apertures can be used, moved by small linear stepper motors. Each stepper motor is controlled for velocity modulation of the respective segment in the manner discussed for single beam systems in said prior publications authored or co-authored by Dr. Plewes.

As an alternative to velocity modulation, simple attenuation of the respective beam segments can be used.

Respective servomechanism can move respective wedge-shaped attenuators into and out of the respective segments of the fan beam to modulate the transmission through the wedge in a feedback scheme of the type discussed above for the case of a single scanning beam.

As yet another alternative, the segments of the fan can be subjected to individual beam width modulation in a feedback arrangement of the type discussed above in the case of using a single scanning beam. For this, the cross-sectional shape and size of each segment of the fan beam can be individually modulated as the segment sweeps across the patient and receptor, in a feedback arrangement such that the segment becomes narrower (its cross-sectional area is less) over thin sections such as the lungs and wider (greater cross-sectional area) over thicker sections such as bone. The segments thus move at the same speed and side-by-side. The beam width modulation can be implemented, as earlier discussed, by individual shutters for the respective segments, which open more or less as the segment scans the patient, in a feedback arrangement using measurements of post-patient radiation in the manner earlier discussed.

As yet another alternative, pulse width modulation can be used for the respective segments of the fan beam, in the manner discussed earlier for a single beam.

In the feedback arrangements for the segments of the fan beam, it can be desirable to use a respective detector, or a respective pair of detectors, for each respective segments, in the manner detector 26 is used in FIG. 1 or detectors D1 and D2 are used in FIG. 4.

I claim:

1. An x-ray machine comprising:
a source of an x-ray beam;
a scanner means to move the beam relative to a patient;
an imaging device which has means to receive x-rays which have been attenuated by the patient during a succession of imaging intervals to form an x-ray image of the patient;
a feedback system for deriving pre-exposure measurements of x-rays attenuated by the patient during a succession of feedback intervals which alternate with said imaging intervals for a single image of the patient and for causing the radiation during the imaging intervals to be modulated as a function of respective pre-exposure measurements, said feedback system comprising an x-ray detector receiving x-rays attenuated by the patient during said feedback intervals and a circuit which modulates the intensity and hardness of the beam during said imaging intervals on the basis of the x-rays attenuated by the patient and received by the detector during respective feedback intervals previous to said imaging intervals.

2. An x-ray machine comprising:
a source of a fan-shaped beam of x-rays;
a scanner means to move the beam relative to a patient in a direction transverse to the plane of the beam;
means to divide said fan-shaped beam into a plurality of individual segments
an imaging device which has means to receive x-rays which have been attenuated by the patient and forms an x-ray image therefrom; and
a plurality of feedback loops, wherein each feedback loop includes a detector for x-rays attenuated by the patient and each feedback loop individually modulates a separate respective segment of the beam by selectively changing the velocity at which the respective beam segment moves relative to the patient.

3. An x-ray machine comprising:
a source of an x-ray beam;
a scanner means to move the x-ray beam relative to a patient;
an imaging device which--has means to receive x-rays which have been attenuated--by the patient and forms an x-ray image of the patient;
a feedback loop which separately measures primary and scattered radiation components of the x-rays attenuated by the patient and modulates the beam on the basis of measurements of the primary and scattered components selected to maintain a constant signal-to-noise ratio in the x-ray image.

4. An x-ray machine comprising:
a source of an x-ray beam;
a scanner which comprises means for moving the x-ray beam relative to a patient along straight raster lines, at constant velocity along a line, said means comprising a rotating pre-patient collimator having a curved slit aperture causing the beam to move relative to the patient along said straight raster lines and at constant velocity along each of said straight lines; and
an imaging device which has means to receive the beam after attenuation thereof by the patient as a post-patient beam during a succession of imaging intervals to form an x-ray image of the patient:
a feedback system having means for deriving pre-exposure measurements of the post-patient beam during a succession of feedback intervals which alternate with said imaging intervals for a single image of the patient and having means for causing the radiation during the imaging intervals to be modulated as a function of respective pre-exposure measurements.

5. An x-ray machine as in claim 1 in which each imaging interval is preceded by two feedback intervals one of which is at a low energy relative to the other and each of which typically has a much shorter duration than the imaging interval.

6. An x-ray machine as in claim 5 in which each pair of feedback intervals is followed by an imaging interval of a duration determined as a function of x-rays attenuated by the patient and received by the feedback loop detector during the pair of feedback intervals.

7. An x-ray machine as in claim 6 in which each pair of feedback intervals is followed by an imaging interval and the beam hardness during the imaging interval is determined as a function of x-rays attenuated by the patient and received by the feedback loop detector during the pair of feedback intervals, wherein beam hardness is raised for high attenuation beam paths and is lowered for low attenuation beam paths during the imaging interval.

8. An x-ray machine as in claim 1 in which the x-ray beam source produces at least one short pulse of radiation during a feedback interval and then, during an imaging interval, a longer pulse of variable duration determined as a function of x-rays attenuated by the patient and received by the feedback loop detector during the short at least one pulse.

9. An x-ray machine as in claim 1 in which the x-ray beam source produces a short pulse of low energy radiation and a short pulse of high energy radiation during a feedback interval and then, during an imaging interval, a longer pulse of a duration determined as a function of x-rays attenuated by the patient and received by the feedback loop detector during the two short pulses.

10. An x-ray machine as in claim 1 in which said x-ray detector is separate from the imaging device which forms the x-ray image, and said x-ray detector scans relative to the patient in at least one dimension.

11. An x-ray machine as in claim 2 in which the separate segments of the fan-shaped beam overlap in part at an imaging plane of the imaging device.

12. An x-ray machine as in claim 3 in which the feedback loop comprises a primary detector which generates a primary signal related to the x-rays attenuated by the patient along the axis of the x-ray beam and a scatter detector which generates a scatter signal related to the x-rays attenuated by the patient off-axis of the x-ray beam.

13. An x-ray machine as in claim 12 in which the imaging device comprises an image intensifier scanned by the x-ray beam.

14. An x-ray machine as in claim 3 including means to vary the photon fluence $N_0$ of the beam from the x-ray beam source incident on the patient so as to maintain the signal-to-noise ratio S/N substantially constant in accordance with the relationship:

$$S/N = (N_0 A T n / (1+R))$$

where T is the patient transmission, A is the pixel size of the x-ray image, n is the quantum efficiency of the imaging device forming the image and R is the ratio of scattered-to-primary photons in the image determined as a function of primary and scattered radiation measured by the feedback loop.

15. An x-ray machine as in claim 4 in which the rotating prepatient collimator comprises a pair of rotating discs each having a spiral aperture slit, and including a second pre-patient collimator having a linear aperture slit, wherein the beam from the x-ray source passes through both the linear slit and one of the spiral slits before impinging on the patient.

16. A method comprising:
scanning an x-ray beam relative to a patient;
forming an x-ray image of the patient on the basis of the beam after attenuation thereof by the patient;
separately measuring primary and scattered post-patient radiation and modulating the beam on the basis of post-patient measurements of primary and scattered radiation to maintain a desired signal-to-noise ratio distribution in the x-ray image.

17. A method as in claim 16 including approximating said image in accordance with a selected measure of a spatial distribution parameter of the beam after attenuation thereof by the patient.

18. An x-ray machine comprising:
a source of a fan - shaped beam of x-rays;
a scanner means to move the beam relative to a patient in a direction transverse to the plane of the beam;
means to divide said fan-shaped beam into a plurality of individual segments;
an imaging device which has means to receive x-rays which have been attenuated by the patient and forms an x-ray image therefrom; and
a plurality of feedback loops, wherein each feedback loop includes a detector for x-rays attenuated by the patient and each feedback loop individually pulse width modulates a separate respective segment of the beam.

* * * * *